(12) United States Patent
Bernard et al.

(10) Patent No.: US 8,920,503 B2
(45) Date of Patent: Dec. 30, 2014

(54) INTERVERTEBRAL IMPLANT INTENDED FOR OSSEOUS FUSION

(75) Inventors: Marc Bernard, Leagman (FR); Philippe Jenny, Pessac (FR); Jean-Charles Lehuec, Pessac (FR)

(73) Assignee: Creaspine (FR)

( * ) Notice: Subject to any disclaimer, the term of this patent is extended or adjusted under 35 U.S.C. 154(b) by 380 days.

(21) Appl. No.: 12/375,128

(22) PCT Filed: Jul. 25, 2007

(86) PCT No.: PCT/FR2007/001272
§ 371 (c)(1),
(2), (4) Date: Jan. 26, 2009

(87) PCT Pub. No.: WO2008/012429
PCT Pub. Date: Jan. 31, 2008

(65) Prior Publication Data
US 2009/0306780 A1 Dec. 10, 2009

(30) Foreign Application Priority Data

Jul. 27, 2006 (FR) .................................. 06 53141
Sep. 22, 2006 (EP) .................................. 06121144

(51) Int. Cl.
*A61F 2/44* (2006.01)

(52) U.S. Cl.
USPC .................................................... 623/17.16

(58) Field of Classification Search
USPC .......................................... 623/17.11–17.16
See application file for complete search history.

(56) References Cited

U.S. PATENT DOCUMENTS

| 5,658,337 | A | * | 8/1997 | Kohrs et al. | 623/17.11 |
| 6,224,631 | B1 | * | 5/2001 | Kohrs | 623/17.11 |
| 2003/0083746 | A1 | * | 5/2003 | Kuslich | 623/17.11 |
| 2003/0139813 | A1 | * | 7/2003 | Messerli et al. | 623/17.11 |
| 2004/0102850 | A1 | * | 5/2004 | Shepard | 623/17.16 |

FOREIGN PATENT DOCUMENTS

| WO | 99/47083 | 9/1999 |
| WO | 03/037229 | 5/2003 |
| WO | 2005/063151 | 7/2005 |

OTHER PUBLICATIONS

International Search Report; PCT/FR2007/001272; Nov. 30, 2007.

* cited by examiner

*Primary Examiner* — Andrew Yang
*Assistant Examiner* — Olivia C Chang
(74) *Attorney, Agent, or Firm* — Cantor Colburn LLP

(57) ABSTRACT

This implant (1) for osseous fusion is intended to be inserted between two adjacent vertebral bodies (4) of a spinal column. It comprises a main body (2) having at least two longitudinal elements of C-shaped contour (2a, 2b) placed back to back and defining:—a solid axis (9), formed by the junction zone of said elements (2a, 2b) and suitable for being positioned parallel to the spinal column and for transmitting the stresses between the two adjacent vertebral bodies, and—at least two longitudinal apertures (6), suitable for holding grafts, oriented outward with respect to said solid axis (9).

15 Claims, 3 Drawing Sheets

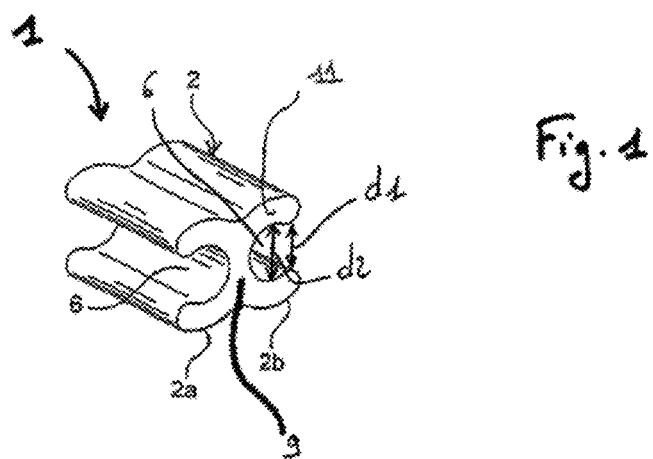
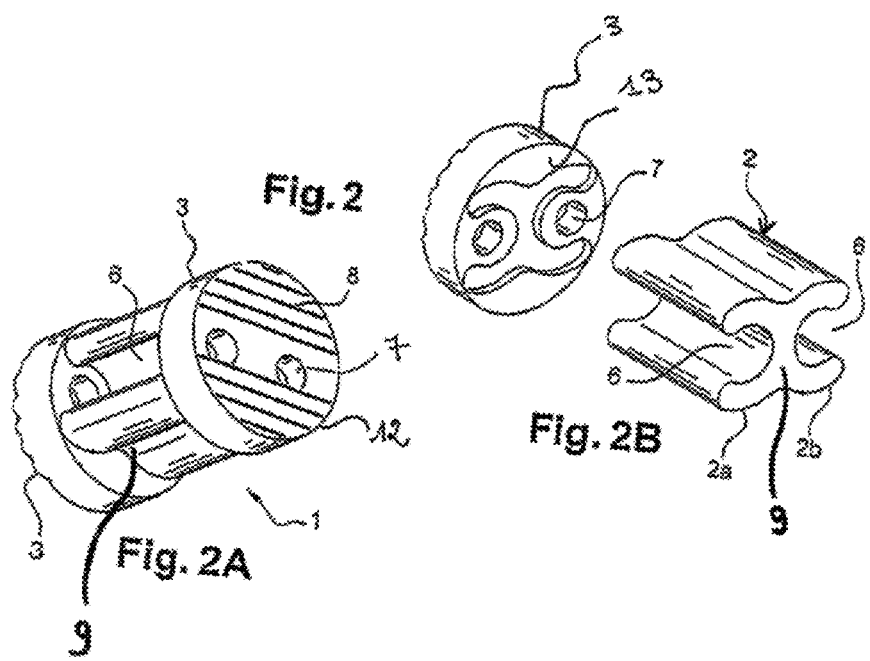

INTERVERTEBRAL IMPLANT INTENDED FOR OSSEOUS FUSION

FIELD OF THE INVENTION

The present invention relates to an intervertebral implant intended for the reconstruction of a vertebral body by insertion of natural or synthetic bone grafts between two vertebral bodies in order to replace a damaged area of the vertebral column or fill an area of deficiency in the vertebral column while allowing a growth of bone cells through and around the implant.

BACKGROUND OF THE INVENTION

These implants must meet several criteria to ensure good stability between two vertebral bodies while allowing a satisfactory fusion rate to be guaranteed. To do this, the implant body which is inserted under pressure between the vertebral bodies must have very high strength along the axis of the vertebral column on the one hand, and a large area of contact with the adjacent vertebral bodies and the residual elements of the vertebral bodies on the other hand.

The implant must have a high mechanical strength relative to the stresses exerted by the vertebral bodies in order to maintain the intervertebral space. Generally speaking, in practice the implant must have a strength 2 to 3 times greater than the forces exerted by the vertebral bodies on the implant. The implant must be resistant at least until bone consolidation.

Generally speaking, the implant is a solid hollow body filled with bone grafts. The walls have openings to allow bone fusion with the vertebral bodies.

The implant is placed between two vertebral bodies, either horizontally in the direction of its thickness or vertically in the direction of its height.

The implant may be classified according to the shape of the body. It may be a parallelepiped of rectangular cross section. In order to adapt better to the shape of the vertebral bodies, it may be ogival or slightly rounded.

It is known for an implant to consist of a cylindrical or oval cage that is hollow inside in order to receive bone grafts, the wall of the cage comprising a set of openings. This type of implant enables a bone fusion around the implant and with the vertebral plates, the center of the grafts conversely not fusing or fusing only partially.

There are also implants comprising only two plates positioned at the ends of an axis. The surgeon is led to fill the implant with compacted grafts all around the axis once the implant is positioned between two vertebral bodies. This type of implant effectively offers a relatively large circumferential area of contact with the external surroundings. However, due to its shape it does not enable the grafts to be kept at the location of the area requiring a bone reconstruction. In addition, the insertion of the grafts into the implant lengthens the operation time.

It would therefore be advantageous for an implant to be available having a very strong structure while having a large and continuous area of contact with the outside for the bone fusion and an optimal holding shape so as to hold the bone grafts.

BRIEF SUMMARY OF THE INVENTION

The present invention proposes an intervertebral implant for bone fusion that is simple in its design and in its mode of operation, and is particularly small and strong to enable better fusion between the bone grafts and the vertebral plates in all directions around the implant.

This implant must be able to be partly filled with bone grafts by the surgeon before the insertion of the implant into the body of the patient. Once inserted into the area to be repaired, this implant is filled completely by the surgeon.

Ideally, the length of the implant should be adjustable so as to be able to adapt this length to the area of deficiency.

Furthermore, the implant should have a solid axis through its shape allowing stresses exerted by the adjacent vertebral bodies to be taken up.

In addition, through its relatively compact shape, the method for manufacturing the implant is very simple to implement.

To this end, the invention relates to an implant for bone fusion intended to be inserted between two adjacent vertebral bodies.

According to the invention, this implant comprises a main body consisting of at least two longitudinal elements of C-shaped cross section placed back to back and thus defining:
 a solid axis, constituted by the joining area of said elements and designed to be positioned parallel to the axis of the vertebral column and to transmit the forces between the two adjacent vertebral bodies; and
 at least two longitudinal recesses, designed for holding grafts, directed outwardly relative to said solid axis.

The ends of the elements in C ensure an optimal area of contact with the adjacent vertebral bodies.

The solid axis formed by the junction between the elements of C-shaped cross section enables an optimum take-up of the forces transmitted by the adjacent vertebral bodies.

The C-shape of the two elements defining the main body allows quick application and excellent holding of bone grafts.

According to other optional features of this implant:
 this implant comprises a bearing surface at each of its ends intended respectively to come into contact with one of said vertebral bodies;
 said bearing surfaces are constituted by the ends of said elements;
 said bearing surfaces are constituted by two plates, each plate comprising at least one orifice opening into one of the longitudinal recesses;
 said elements and said plates form a one-piece part;
 said elements and said plates form distinct parts, said plates each comprising a coupling face capable of cooperating with one end of said elements and a bearing face capable of coming into contact with one of said vertebral bodies;
 said bearing surfaces comprise projections designed to strengthen the bearing on the vertebral bodies;
 said elements have a longitudinal size of between approximately 16 mm and 90 mm and a diameter of between approximately 10 and 36 mm;
 this implant comprises, at at least one of its ends, a coupling surface capable of cooperating with a joining element, said joining element being designed to enable the assembly of implants with one another;
 said solid axis comprises at least one opening so as to create a communication between the two longitudinal recesses;
 this implant is made of a biocompatible material, said main body being made of a radiotransparent material;
 said plates are made of a radiopaque material;
 this implant comprises positioning means produced at the ends of said elements, these means being designed respectively to cooperate with the arms of a distractor, the design of said positioning means being suited to the design of these arms such that said end is able to slide during removal of said distractor and such that the ends of said implant are in direct contact with the adjacent vertebral bodies separated by said arms during fitting of the implant; and said positioning means comprise a groove.

The invention also relates to a method for producing an implant, described above, consisting of at least two C-shaped elements.

BRIEF DESCRIPTION OF THE SEVERAL VIEWS OF THE DRAWINGS

The invention will be described in greater detail with reference to the appended drawings, in which:

FIG. 1 shows an angled view of an implant according to the invention;

FIG. 2 shows the implant of FIG. 1 adjacent a plate and coupling face;

FIG. 2.A shows a particular embodiment of the implant of FIG. 1 comprising plates at its ends, and FIG. 2.B shows an exploded view of the assembly of the plates and the main body;

DETAILED DESCRIPTION OF THE INVENTION

Figure 3:
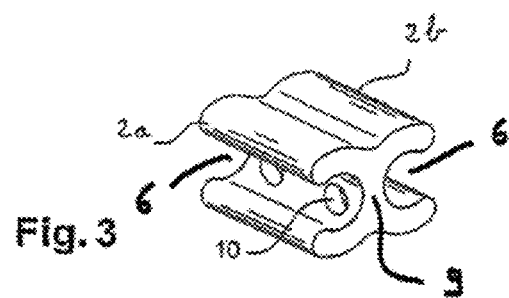
FIG. 3 shows another particular form of the implant from FIG. 1.

FIG. 1 shows an implant 1 according to the invention.

This implant comprises a main body 2 consisting of two longitudinal elements of C-shaped cross section 2a, 2b placed back to back, the assembly defining two longitudinal recesses 6 designed to hold grafts.

The joining area of these two elements of C-shaped cross section defines a solid axis 9 constituted by the walls of these elements in contact.

This solid axis 9, which is designed to be positioned generally parallel to the axis of the vertebral column, enables effective take-up of the stresses exerted by the vertebral bodies on the implant.

"C-shaped cross section" means that in cross section, i.e. taken perpendicular to the solid axis 9, each element 2a, 2b has the shape of the letter "C".

More precisely, and as indicated in FIG. 1, this means that the distance d1 between the two ends of the branches of the "C" is less than the distance d2 between the median areas (i.e. approximately midway between the base of the "C" and said ends) of these two branches.

The ends 11 of the elements 2a, 2b directly constitute bearing surfaces for the implant designed to come into contact with the adjacent vertebral bodies 4.

In addition, each recess 6 comprises a longitudinal opening directed outwardly relative to the solid axis 9, thus allowing the grafts to be in circumferential and continuous contact with the external surroundings.

Moreover, this particularly advantageous form of the implant enables the main body to be obtained by a method that is simpler and less costly in relation to implants of conventional form.

The method for manufacturing such an implant may be an extrusion method in which hot extrusion-pressing of a plastic material is carried out. The material is formed through an extrusion die having a shape complementary to that of the implant to form a continuous piece.

Implants of various lengths are then obtained by cutting the continuous piece. The implant of FIG. 1 does not require any additional machining step or other process.

Of course, a conventional implant manufacturing method by machining is also conceivable.

FIG. 2.A shows another embodiment of the implant in which the bearing surface of the implant is constituted by two plates 3 situated at the ends of the main body 2 and the bearing surface is one of the two faces 12 of the plate.

In order to encourage bone fusion with the adjacent vertebral bodies, FIG. 2.A shows that the plates 3 contain orifices 7 located opposite the ends of the longitudinal recesses 6 in order to have an area of contact between the grafts held in the longitudinal recesses and the adjacent vertebral bodies to encourage bone fusion in a vertical direction.

The plates 3 and the elements 2a, 2b may be formed from a single-piece part or formed from distinct elements.

FIG. 2.B shows an assembly of one of the two plates and the main body 2. The plate 3 comprises a coupling face 7 capable of cooperating with the end of the main body 2 formed by the two elements 2a, 2b and a bearing face 12 designed to come into contact with the vertebral body.

The plate 3 and the end of the main body 2 are thus advantageously connected to each other in a removable manner to enable the length of the implant to be varied and thus this implant to be matched to the area of the vertebral column to be repaired.

Thus the main bodies can be placed end-to-end and assembled using joining elements. In this context, a main body lying at one end of the implant is connected to another single main body by a single joining element.

Conversely, an intermediate main body is connected to two other main bodies by two joining elements mounted on each side of the ends of this intermediate main body. Each joining element comprises two coupling faces allowing each end of a main body to be accommodated.

These coupling faces have a profile complementing the profile of the main body, but they may have any other shape enabling the main bodies to be locked when placed end-to-end.

Thus the number of main bodies constituting an implant is not limiting in the two embodiments described above.

It is possible, for example, to obtain an implant 64 mm in length by placing together end-to-end four main bodies each having a length of 16 mm.

Whether or not the elements of C-shaped cross section are identical, they have a longitudinal size, i.e. measured between the two ends of C-shaped cross section, preferably between approximately 16 mm and 90 mm and a diameter between 10 and 36 mm.

Advantageously, the number of elements of C-shaped cross section forming a main body is not limiting.

Advantageously, the profile of the implant thus obtained conforms to the anatomical curvature of the vertebral column.

Each element of C-shaped cross section may in addition comprise mechanical locking devices enabling the coupling faces of joining elements to be locked in the coupled position. These locking devices are, for example, screws.

Advantageously, the ends 11 of the elements 2a, 2b and the bearing faces 12 of the plates 3 comprise a set of projections 8 designed to strengthen the bearing on the vertebral body and to avoid transverse movement of the implant into the intervertebral space. These projections 8 consist, for example, of notches or of a series of asperities.

FIG. 3 shows another embodiment of the main body 2 in which openings 10 are made in the solid axis 9 constituted by the outer walls of the elements of C-shaped cross section 2a, 2b in contact so as to create communication between the two longitudinal recesses. This communication between the recesses promotes the quality of the graft and enables a single unique fused block to be obtained.

In order to insert the implant between two adjacent vertebral bodies, two adjacent vertebral bodies are first of all separated by means of a distractor equipped with two arms enabling an intervertebral space to be obtained.

The implant is then positioned between the two arms in the direction of the height of the main body in this space. The arms are then removed so as not to displace the implant.

Figure 4:
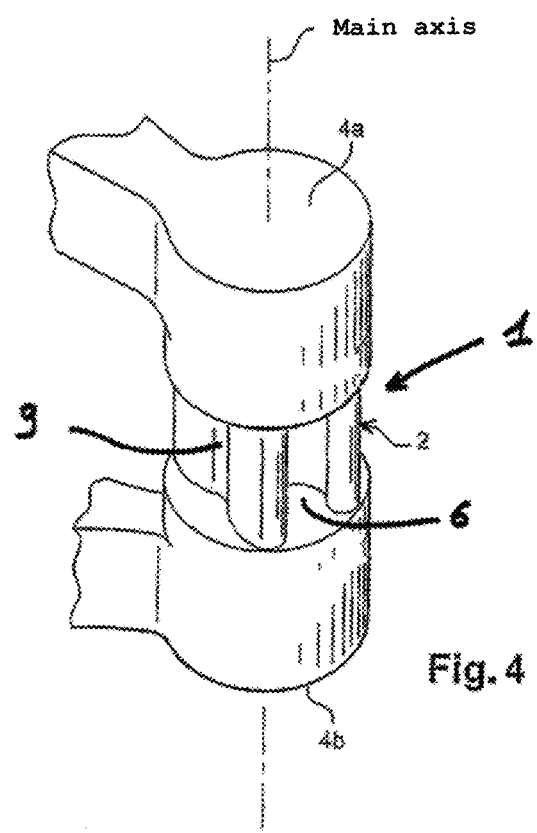
FIG. 4 is a schematic representation of the implant of FIG. 1 inserted between two vertebral bodies.

FIG. 4 schematically shows an implant 1 produced according to the invention positioned between two vertebral bodies. In this figure, the reference "main axis" designates the general direction of the vertebral column and it can be seen that the solid axis 9 of the main body.

To increase the stability and the rigidity of the mounting, a posterior and/or anterior osteosynthesis is carried out by a screw between the overlying vertebral body 4a and the underlying vertebral body 4b in relation to the implant 1.

In another, particularly advantageous form of the invention, the implant comprises a groove 14 effected in the bearing surface 9, 12. This groove, cooperating with the end of each distractor arm, enables, on the one hand, the implant to be placed between two vertebral bodies by putting the bearing surface 9, 12 of the implant into direct contact with the adjacent vertebral bodies, thus avoiding an over-distraction of the vertebral bodies, and, on the other hand, effective removal of the ends of the arms during removal of said distractor, so as not to displace the initially positioned implant.

Figure 5:
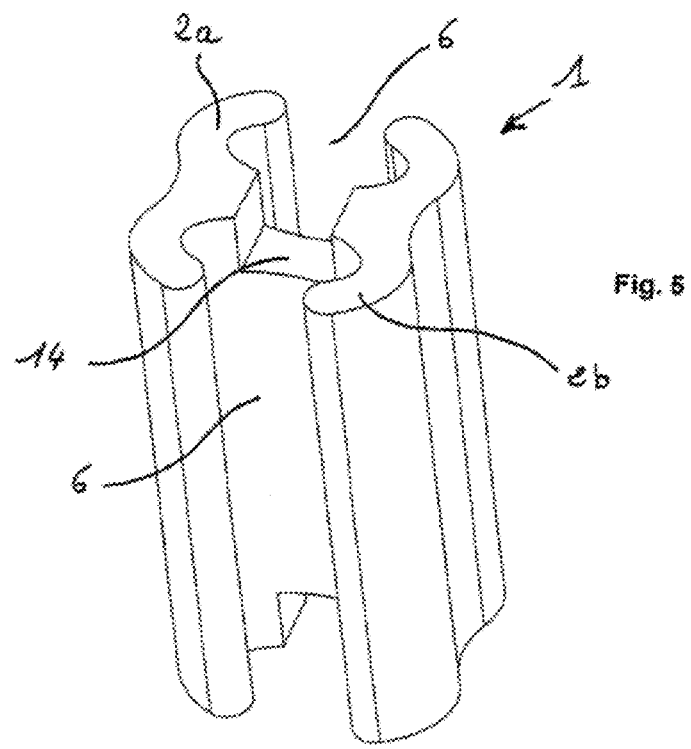
FIG. 5 is a schematic representation of the implant of FIG. 1 comprising a groove at its ends.

FIG. 5 shows the case in which the groove is produced directly in the ends of the elements of C-shaped cross section 2a, 2b.

Figure 6:
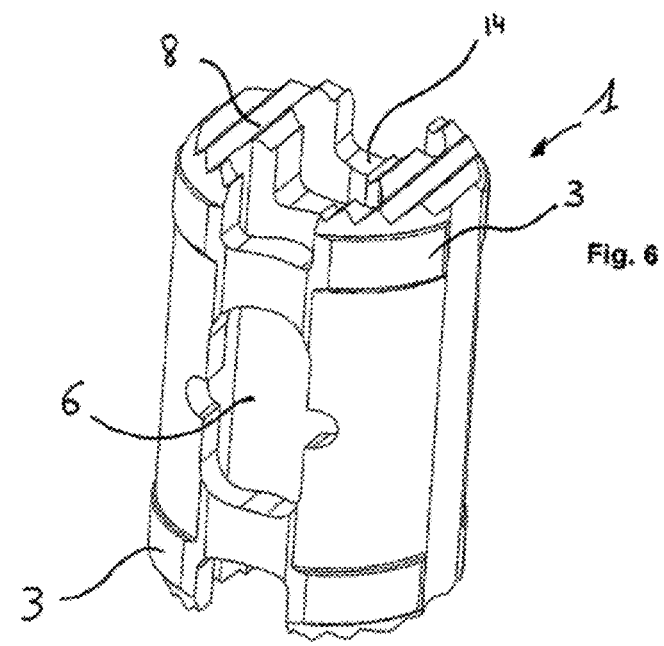
FIG. 6 is a schematic representation of the implant of FIG. 2 comprising a groove in the plates.

FIG. 6 shows the case in which the groove is produced in the plates 3.

Advantageously, the implant may be partly filled before being positioned in the intervertebral space. But the longitudinal recesses may also be completely filled, allowing a reduction in operation time.

Moreover, the effect of holding grafts within longitudinal recesses, obtained thanks to the C-shaped cross section of the elements 2a, 2b makes the operation of putting the grafts in place easier and makes the positioning of the grafts in the area to be repaired more precise.

Advantageously, the particular form of the implant enables the stresses exerted by the vertebral bodies to be distributed over the walls of the elements and over the solid axis 9 constituted by the walls of the elements 2a, 2b that are joined. The effectiveness of this takeup of forces may be increased by adding excessive thickness to the solid axis 9.

The implant is made of a biocompatible material. The main body 2 is preferably made of a radiotransparent material, thus enabling the evolution of the bone fusion and the bone consolidation in the patient to be tracked. The material used is generally made of a polymer, for example a material from the polyaryletheretherketone (PEEK) family. The modulus of elasticity of the material is preferably close to that of bone in order to avoid stress-induced deviation.

The plates 3 are preferably made of a radiopaque material so as to be able to spot the location of the implant through a radiological image.

The invention claimed is:

1. An implant for bone fusion intended to be inserted between two adjacent vertebral bodies of a vertebral column, comprising:
 a main body including at least two longitudinal elements of C-shaped cross section placed back to back and forming a continuous concave curvature between said longitudinal elements, each longitudinal element having a first end and a second end, wherein the continuous concave curvature extends from the first end of a first longitudinal element to the first end of a second longitudinal element; wherein a first distance between each of the first end and the second end is less than a second distance between a first median and a second median of each respective longitudinal element; wherein each longitudinal element further includes at least one longitudinal edge having a smooth surface;
 a solid axis, constituted by a joining area of said longitudinal elements and designed to be positioned parallel to an axis of the vertebral column and to transmit the forces between the two adjacent vertebral bodies; and
 at least two longitudinal recesses, designed for holding grafts, directed outwardly relative to said solid axis.

2. The implant as claimed in claim 1, wherein the implant comprises a bearing surface at each of the implant's ends intended respectively to come into contact with one of said vertebral bodies.

3. The implant as claimed in claim 2, wherein said bearing surfaces are constituted by the ends of said elements.

4. The implant as claimed in claim 2, wherein said bearing surfaces are constituted by two plates, each plate comprising at least one orifice opening into one of the longitudinal recesses.

5. The implant as claimed in claim 4, wherein said longitudinal elements and said plates form a one-piece part.

6. The implant as claimed in claim 4, wherein said longitudinal elements and said plates form distinct parts, said plates each comprising a coupling face capable of cooperating with one end of said longitudinal elements and a bearing face capable of coming into contact with one of said vertebral bodies.

7. The implant as claimed in claim 2, wherein said bearing surfaces comprise projections designed to strengthen a bearing on the vertebral bodies.

8. The implant as claimed in claim 1, wherein said longitudinal elements have a longitudinal size of between approximately 16 mm and 90 mm and a diameter of between approximately 10 and 36 mm.

9. The implant as claimed in claim 1, wherein the implant comprises, at at least one of its ends, a coupling surface capable of cooperating with a joining element, said joining element being designed to enable assembly of implants with one another.

10. The implant as claimed in claim 1, wherein said solid axis comprises at least one opening so as to create a communication between the two longitudinal recesses.

11. The implant as claimed in claim 1, wherein the implant is made of a biocompatible material, said main body being made of a radiotransparent material.

12. The implant as claimed in claim 4, wherein said plates are made of a radiopaque material.

13. The implant as claimed in claim 1, wherein the implant comprises positioning means produced at ends of said longitudinal elements, designed respectively to cooperate with arms of a distractor, a design of said positioning means being suited to a design of the arms such that said end is able to slide during removal of said distractor and such that ends of said implant are in direct contact with adjacent vertebral bodies separated by said arms during fitting of the implant.

14. The implant as claimed in claim 13, wherein said positioning means comprise a groove.

15. A method for producing said main body of the implant as claimed in claim 1, wherein the method comprises the following steps:
   obtaining a part by continuous extrusion from an extrusion die having a shape complementary to that of said main body comprising at least two C-shaped elements;
   cutting said part to obtain main bodies of various lengths.

* * * * *